United States Patent [19]

Aoki et al.

[11] 4,430,423
[45] Feb. 7, 1984

[54] COLOR PHOTOGRAPHIC LIGHT-SENSITIVE MATERIAL

[75] Inventors: Kozo Aoki; Michio Ono, both of Kanagawa, Japan

[73] Assignee: Fuji Photo Film Co., Ltd., Minami-Ashigara, Japan

[21] Appl. No.: 451,229

[22] Filed: Dec. 20, 1982

[30] Foreign Application Priority Data

Dec. 18, 1981 [JP] Japan .................. 56-204746

[51] Int. Cl.$^3$ .................. G03C 7/16; G03C 7/26
[52] U.S. Cl. .................. 430/384; 430/385; 430/393; 430/505; 430/558
[58] Field of Search .............. 430/384, 385, 505, 558, 430/393

[56] References Cited

U.S. PATENT DOCUMENTS

| | | | |
|---|---|---|---|
| 3,244,520 | 4/1966 | Schulte et al. | 430/384 |
| 4,029,508 | 6/1977 | Tanaka et al. | 430/558 |
| 4,078,936 | 3/1978 | Masuda et al. | 430/558 |
| 4,233,399 | 11/1980 | Kitzing et al. | 430/558 |
| 4,327,173 | 4/1982 | Aoki et al. | 430/558 |

Primary Examiner—J. Travis Brown
Attorney, Agent, or Firm—Sughrue, Mion, Zinn, Macpeak & Seas

[57] ABSTRACT

A color photographic light-sensitive material comprising a cupport having coated thereon at least one silver halide emulsion layer. The color photographic light-sensitive material contains a cyan dye forming coupler represented by the following general formula (I):

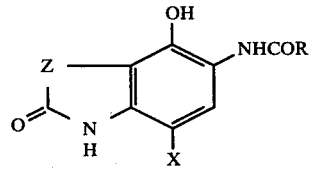

wherein Z represents

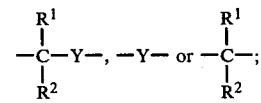

R represents a substituted or unsubstituted alkyl group, a substituted or unsubstituted aryl group or a substituted or unsubstituted heterocyclic group; X represents a hydrogen atom or a group capable of being released upon an oxidative coupling reaction with a developing agent; Y represents

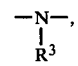

—O— or —S—; $R^1$ and $R^2$, which may be the same or different, each represents a halogen atom, a substituted or unsubstituted alkyl group, a substituted or unsubstituted aryl group, a substituted or unsubstituted alkoxy group, a substituted or unsubstituted alkoxycarbonyl group, a substituted or unsubstituted alkylcarbonyl group, a substituted or unsubstituted arylcarbonyl group, a substituted or unsubstituted carbonyl group, a substituted or unsubstituted acylamino group or a nitryl group or $R^1$ and $R^2$ together represents an oxo group; and $R^3$ represents a hydrogen atom, a substituted or unsubstituted alkyl group or a substituted or unsubstituted aryl group.

The color photographic light-sensitive material provides a cyan color image having preferred spectral absorption characteristics for color reproduction and excellent fastness to light and heat. Furthermore, a decrease in optical density of the cyan color image is not substantially observed even when the color photographic light-sensitive material is processed with a bleaching solution which has a weak oxidation power or a bleaching solution which is exhausted.

19 Claims, No Drawings

COLOR PHOTOGRAPHIC LIGHT-SENSITIVE MATERIAL

FIELD OF THE INVENTION

The present invention relates to a color photographic light-sensitive material containing a novel cyan dye forming coupler.

BACKGROUND OF THE INVENTION

When color development is carried out after a silver halide photographic light-sensitive material is exposed to light, an oxidized aromatic primary amine developing agent reacts with a dye forming coupler to form a color image. In this process, color reproduction by a subtractive process is generally utilized. In accordance with this process, dye images of cyan, magenta and yellow, which are complement colors of red, green and blue, respectively, are formed in order to produce images of red, green and blue. For example, phenol derivatives or naphthol derivatives are mainly used as cyan color image forming couplers.

However, the color images formed from conventionally employed phenol derivatives or naphthol derivatives have some problems with respect to durability. For example, color images formed from the 2-acylaminophenol cyan couplers as described in U.S. Pat. Nos. 2,367,531 and 2,423,730 generally have inferior fastness to heat. Color images formed from the 2,5-diacylaminophenol cyan couplers as described in U.S. Pat. Nos. 2,369,929 and 2,772,162 generally have inferior fastness to light, and color images formed from 1-hydroxy-2-naphthamide cyan couplers generally have inferior fastness to both light and heat.

Further, with respect to the 1-hydroxy-2-acylaminocarbostyryl cyan couplers as described in Japanese Patent Application (OPI) No. 104333/81, spectral absorption characteristics of color images formed therefrom are not preferable with respect to color reproduction, while the color images formed are superior in fastness to both light and heat.

SUMMARY OF THE INVENTION

It is an object of the present invention to provide a color photographic light-sensitive material containing a cyan dye forming coupler which forms color images wherein the disadvantages in fastness and color reproduction are eliminated.

Another object of the present invention is to provide a coupler which does not substantially decrease in optical density when a color photographic light-sensitive material containing the coupler is processed with a bleaching solution which has a weak oxidation power, for example, a bleach solution containing sodium iron (III) ethylenediaminetetraacetate, ammonium iron (III) ethylenediaminetetraacetate, etc. or a bleaching solution which is exhausted.

Other objects of the present invention will become apparent from the following detailed description and examples.

These objects of the present invention have been accomplished by using a cyan dye forming coupler represented by the following general formula (I):

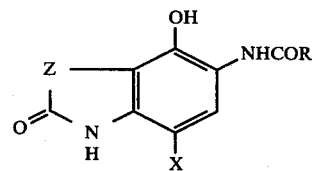

wherein Z represents

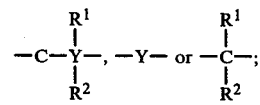

R represents a substituted or unsubstituted alkyl group, a substituted or unsubstituted aryl group or a substituted or unsubstituted heterocyclic group; X represents a hydrogen atom or a group capable of being released upon an oxidative coupling reaction with a developing agent; Y represents

—O— or —S—; $R^1$ and $R^2$, which may be the same or different, each represent a halogen atom, a substituted or unsubstituted alkyl group, a substituted or unsubstituted aryl group, a substituted or unsubstituted alkoxy group, a substituted or unsubstituted alkoxycarbonyl group, a substituted or unsubstituted alkylcarbonyl group, a substituted or unsubstituted arylcarbonyl group, a substituted or unsubstituted carbamoyl group, a substituted or unsubstituted acylamino group or a nitrile group or $R^1$ and $R^2$ together represents an oxo group; and $R^3$ represents a hydrogen atom, a substituted or unsubstituted alkyl group or a substituted or unsubstituted aryl group.

DETAILED DESCRIPTION OF THE INVENTION

Preferred embodiments of R, Z and X in the above general formula (I) will now be described in greater detail below.

In the general formula (I), R represents a straight chain or cyclic alkyl group, preferably an alkyl group having from 1 to 22 carbon atoms (for example, a methyl group, a butyl group, a pentadecyl group, a cyclohexyl group, etc.), an aryl group (for example, a phenyl group, a naphthyl group, etc.), or a heterocyclic group (for example, a 2-pyridyl group, a 2-furyl, a 2-oxazolyl group, etc.). These groups can be substituted with one or more substituents selected from an alkyl group, an aryl group (for example, a phenyl group, a naphthyl group, etc.), an alkoxy group (for example, a methoxy group, a myristyloxy group, a methoxyethoxy group, etc.), an aryloxy (for example, a phenoxy group, a 2,4-di-tert-amylphenoxy group, a 3-tert butyl-4-hydroxyphenoxy group; a naphthoxy group, etc.), a carboxy group, an alkylcarbonyl group (for example, an acetyl group, a tetradecanoyl group, etc.), an arylcarbonyl group (for example, a benzoyl group, etc.), an alkoxycarbonyl group (for example, a methoxycarbonyl group, a benzyloxycarbonyl group, etc.), an aryloxycarbonyl group (for example, a phenoxycarbonyl group, a p-tolyloxycarbonyl group, etc.), an acyloxy group (for example, an acetyloxy group, a benzoyloxy group, a phenylaminocarbonyloxy group, etc.), a sulfamoyl group (for example, an N-ethylsulfamoyl group, an N-octadecylsulfamoyl group, etc.), a carbamoyl group (for example, an N-ethylcarbamoyl group, an N-methyl-N-dodecylcarbamoyl group, etc.), a sulfonamido group (for example, a methanesulfonamido group, a benzenesulfonamido group, an ethylaminosulfonamido group, etc.), an acylamino group (for example, an acetylamino group, a benzamido group, an ethoxycarbonylamino group, a phenylaminocarbonylamino group, etc.), a diacylamino group (for example, a succinimido group, a hydantoinyl group, etc.), a sulfonyl group, (for example, a methanesulfonyl group, etc.), a hydroxy group, a cyano group, a nitro group and a halogen atom.

In the general formula (I), Z represents a group selected from

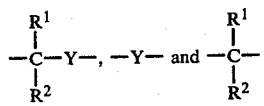

wherein Y represents

—O— or —S—. $R^1$ and $R^2$, which may be the same or different, each represents a hydrogen atom, a halogen atom, an alkyl group (for example, a methyl group, a butyl group, etc.), an aryl group (for example, a phenyl group, a naphthyl group, etc.), an alkoxy group (for example, a methoxy group, a dodecyloxy group, etc.), an alkoxycarbonyl group (for example, a methoxycarbonyl group, a tetradecyloxycarbonyl group, etc.), an alkylcarbonyl group (for example, an acetyl group, a butanoyl group, etc.), an arylcarbonyl group (for example, a benzoyl group, etc.), a carbamoyl group (for example, an N-ethylcarbamoyl group, etc.), an acylamino group (for example, an acetylamino group, an N-methylbenzoylamino group, etc.) or a nitrile group, or $R^1$ and $R^2$ together represents an oxo group. $R^3$ represents a hydrogen atom, an alkyl group (for example, a methyl group, a butyl group, an octyl group, etc.) or an aryl group (for example, a phenyl group, etc.) $R^1$, $R^2$ and $R^3$ may be substituted with one or more of the substituents as described for R above.

In the general formula (I), X represents a hydrogen atom or a coupling-off group. Examples of the coupling-off groups include, for example, a halogen atom (for example, a chlorine atom, etc.), an alkoxy group (for example, an ethoxy group, a dodecyloxy group, a methoxyethylcarbamoylmethoxy group, a carboxymethoxy group, an ethylsulfonylethoxy group, etc.), an aryloxy group (for example, a phenoxy group, a naphthoxy group, etc.), an acyloxy group (for example, an acetoxy group, a tetradecanoyloxy group, a benzoyloxy group, etc.), a sulfonyloxy group (for example, a methanesulfonyloxy group, a toluenesulfonyloxy group, etc.), an acylamino group (for example, a dichloroacetylamino group, a heptafluorobutyrylamino group, etc.), a sulfonylamino group (for example, a methanesulfonylamino group, a toluene sulfonylamino group, etc.), an alkoxycarbonyloxy group (for example, an ethoxycarbonyloxy group, a benzyloxycarbonyloxy group, etc.), an aryloxycarbonyloxy group (for example, a phenoxycarbonyloxy group, etc.), an imino group (for example, a succinimido group, a hydantoinyl group, etc.), and the like.

More specifically, compounds represented by the following general formulae (II), (III), (IV) and (V) are preferred.

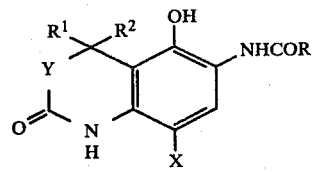

[II]

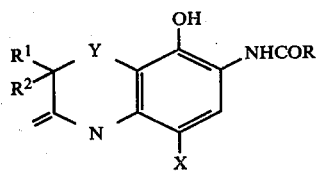

[III]

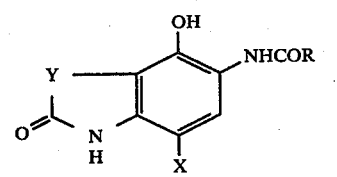

[IV]

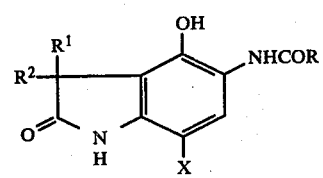

[V]

In the general formulae (II) to (V) above, R, $R^1$, $R^2$, Y and X each has the same meaning as defined in the general formula (I). In these formulae, an alkyl group and an aryl group are particularly preferred for R,

and —O— are particularly preferred for Y, a hydrogen atom, an alkyl group and an aryl group are particularly preferred for each of $R^1$, $R^2$ and $R^3$, and a hydrogen atom and a chlorine atom are particularly preferred for X.

It is believed that the compounds represented by the general formula (I) described above have various preferred characteristics owing to the ring fused on the 5- and 6-positions of the phenol. Further, the compounds represented by the general formula (I) are similar in their chemical structures to the compounds described in Japanese Patent Application (OPI) No. 104333/81. However, it is surprising that the particularly preferred characteristics are obtained by reducing one carbon atom or replacing one carbon atom with one hetero atom in the fused ring.

More specifically, the compounds represented by the general formula (I) have preferred characteristics. For example, they have a good solubility to an organic solvent having a high boiling point and are stable under a dispersed condition in a photographic emulsion. In addition, the spectral absorption characteristics of color images obtained therefrom are excellent and the color images obtained have a good fastness to light and heat.

Examples of the couplers included in the scope of the present invention are set forth below, but the present invention is not to be construed as being limited thereto.

-continued

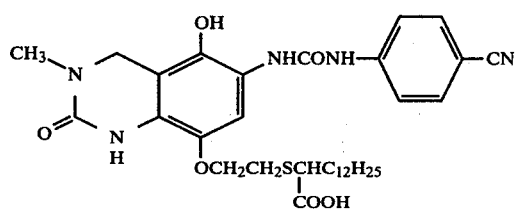

(17)

Representative synthesis examples of the couplers according to the present invention are specifically set forth below.

SYNTHESIS EXAMPLE 1

Synthesis of 7-Chloro-4-hydroxy-5-[2-(2,4-di-tert-amylphenoxy)-butanamido]-2,3-dihydro-1,3-benzimidazol-2-one [Coupler (1)]

Step (i): Synthesis of 5-Amino-4-chloro-2-[2-(2,4-di-tert-amylphenoxy)butanamido]phenol 20 g of 2-amino-4-chloro-5-nitrophenol was dispersed in 150 ml of acetonitrile to which 37.7 g of 2-(2,4-di-tert-amylphenoxy)butanoyl chloride was added dropwise under refluxing. After refluxing for 4 hours, the reaction mixture was cooled to deposit crystals. The crystals were collected by filtration, washed with acetonitrile and dried to yield 49.5 g thereof. 49 g of the crystals were refluxed with stirring for 1 hour together with 28 g of reduced iron powder, 2.7 g of ammonium chloride, 50 ml of water and 500 ml of isopropanol. After removing the iron powder by filtration, the filtrate was cooled to deposite the crystals. The crystals were collected by filtration and dried to obtain 42.4 g of the above described compound.

Step (ii): Synthesis of 5-Ethoxycarbonylamino-4-chloro-2-[2-(2,4-di-tert-amylphenoxy)butanamido]-phenol 42 g of the 5-amino-4-chloro-2-[2-(2,4-di-tert-amylphenoxy)butanamido]phenol obtained in Step (i) above was dispersed in acetonitrile to which 10.4 g of ethyl chloroformate was added dropwise under refluxing. After refluxing for 3 hours, the reaction mixture was cooled to deposite crystals. The crystals were collected by filtration and dried to obtain 41.8 g of the above described compound.

Step (iii): Synthesis of 7-Chloro-4-hydroxy-5-[2-(2,4-di-tert-amylphenoxy)butanamido]-2,3-dihydro-1,3-benzimidazol-2-one 41 g of the 5-ethoxycarbonylamino-4-chloro-2-[2-(2,4-di-tert-amylphenoxy)butanamido]phenol obtained in Step (ii) above was dispersed in 50 ml of acetic acid to which a mixture solution of 5 ml of fuming nitric acid and 5 ml of acetic acid was added dropwise at a temperature of 5° C. After stirring for 2 hours at 5° C., the reaction mixture was poured into water and the crystals thus deposited were collected by filtration and washed with water. After drying 33.2 g of the crystals were obtained. The crystals were dispersed in 400 ml of water and heated with stirring. To the mixture, 100 g of sodium hydrosulfite divided into several portions was gradually added and further heated with stirring for about 30 minutes. After completion of the reaction, the reaction solution was cooled with ice and the crystals thus deposited were collected by filtration and washed with water. After drying 27.4 g of the crystals were obtained. 27 g of the crystals were dissolved in 50 ml of toluene to which was added 1 g of p-toluenesulfonic acid. After refluxing for about 5 hours with stirring, the mixture was cooled to room temperature. The reaction solution was washed with water and the solvent was distilled off under a reduced pressure. The residue was recrystallized from acetonitrile to obtain 14 g of the above described coupler, having a melting point of 201° to 204° C.

Elemental Analysis: Calculated: C: 64.46%, H: 7.41%, N: 8.35%. Found: C: 64.52% H: 7.44%, N: 8.44%.

SYNTHESIS EXAMPLE 2

Synthesis of 5-Hydroxy-6-pentadecafluorooctanoylamino-8-chloro-1,2,3,3-tetrahydro-4,1-benzoxazin-2-one [Coupler (7)]

Step (i): Synthesis of 2-Amino-4-chloro-5-methoxyphenol 150 g of 1-methoxyphenol was dissolved in 600 ml of chloroform to which 171.2 g of sulfuryl chloride was gradually added dropwise at a temperature of 5° C. After stirring for about 2 hours at 5° C., the reaction mixture was washed with water and the solvent was distilled off under reduced pressure to obtain 190 g of the oily product. The oily product was dissolved in chloroform to which 80 ml of fuming nitric acid was gradually added dropwise at 5° C. After stirring for about 1 hour at 5° C., the reaction mixture was washed with water and the solvent was distilled off under reduced pressure. The residue was separated by a column charactography (using a silica gel and a solvent mixture of ethyl acetate and chloroform as a spreading agent) to obtain 82 g of the nitro compound as a solid product. 82 g of the nitro compound was dispersed in 800 ml of water and 200 ml of methanol and heated with stirring. To the mixture, 350 g of sodium hydrosulfite divided into several portions was gradually added and further heated with stirring for about 30 minutes. After the completion of the reaction, the reaction solution was cooled with ice and the crystals thus deposited were collected by filtration and washed with water. After drying 66 g of the above described compound was obtained.

Step (ii): Synthesis of 2-Methyl-5-chloro-6-amino-7-methoxybenzoxazole 65 g of the 2-amino-4-chloro-5-methoxyphenol obtained in Step (i) above was dispersed in 100 ml of acetonitrile to which 40 g of acetic anhydride was added dropwise under refluxing. After refluxing for 3 hours, the reaction mixture was cooled to deposit the crystals. The crystals were collected by filtration and dried to yield 75 g thereof. 75 g of the crystals were suspended in 150 ml of toluene to which was added 10 g of p-toluene sulfonic acid. After refluxing for 3 hours, the reaction mixture was washed with water and the toluene was distilled off under a reduced pressure. The residue was recrystallized from acetonitrile and dried to yield 61 g thereof. 61 g of the crystals were dissolved in 100 ml of concentrated sulfuric acid and 40 ml of acetic anhydride and cooled to a temperature of 5° C. To the mixture 20.5 ml of fuming nitric acid was gradually added dropwise with stirring and the mixture was further stirred for 1 hour at 5° C. After the completion of the reaction, the reaction mixture was poured into ice water to deposit the crystals. The crystals were collected by filtration and separated by column chromatography (using a silica gel and a solvent mixture of ethyl acetate and chloroform as a spreading agent) to obtain 31 g of the nitro compound as crystals. 30 g of the nitro compound was refluxed with stirring for 1 hour together with 35 g of reduced iron powder, 3.3 g of ammonium chloride, 50 ml of water and 500 ml of isopropanol. After removing the iron powder by filtration, the filtrate was cooled to deposite the crystals. The crystals were collected by filtration and dried to obtain 23.6 g of the above described compound.

Step (iii): Synthesis of 5-Hydroxy-6-pentadecafluorooctanoylamino-8-chloro-1,2,3,3-tetrahydro-4,1-benzoxazin-2-one 23 g of the crystals obtained in Step (ii) above was dispersed in 100 ml of acetonitrile to which 12.8 g of chloroacetic chloride was added dropwise under refluxing. After further refluxing for 3 hours, the reaction mixture was cooled and poured into water to deposit the crystals. The crystals were collected by filtration and dried to yield 28.1 g thereof. To 28 g of the crystals was added 14 g of anhydrous aluminium chloride and heated to a temperature of 130° C. Then 14 g of anhydrous aluminium chloride was added and the mixture was further stirred at 150° to 160° C. for 1.5 hours. The reaction mixture was poured into ice water. The crystals thus deposited were collected by filtration and stirred in a 7.5% aqueous sodium hydroxide solution for 30 minutes. The reaction solution was neutralized with acetic acid and the crystals thus deposited were collected to yield 21 g thereof. The crystals were recrystallized from acetonitrile to obtain 15 g of the crystals. 15 g of the crystals were dispersed in 120 ml of ethanol to which was added 40 ml of 6 N hydrochloric acid and heated with stirring for 5 hours. The reaction mixture was poured into water and neutralized with sodium hydrogen carbonate to deposit the crystals. The crystals were collected by filtration and recrystallized with acetonitrile to yield 8.1 g thereof. 8 g of the crystals were dispersed in acetonitrile to which was added dropwise 17 g of pentadecafluorooctanol chloride under refluxing. After further refluxing with stirring for 3 hours, the reaction mixture was poured into water to deposit the crystals. The crystals were collected by filtration and recrystallized to obtain 16 g of the above described coupler.

Elemental Analysis: Calculated: C: 31.47% H: 9.90%, N: 4.59%. Found: C: 31.51%, H: 9.93%, N: 4.70%.

SYNTHESIS EXAMPLE 3

Synthesis of 8-Chloro-5-hydroxy-6-(2-dodecanesulfonamidobenzoylamino)-1,2,3,4-tetrahydro-3-methylquinazolin-2-one [Coupler (11)]

Step (i): Synthesis of 2-Dodecanesulfonamidobenzoyl chloride

To a mixture of 90.6 g of anthranilic acid methyl ester, 85 g triethylamine, and 500 ml of toluene was added 107.5 g of dodecanesulfonic acid at 15° C. After stirring for 2 hours, the reaction mixture was washed with diluted hydrochloric acid and then a saturated aqueous sodium chloride solution. The solvent was distilled off under a reduced pressure and to the residue were added 500 ml of methanol and a solution containing 64 g of sodium hydroxide dissolved in 100 ml of water. The mixture was heated for 1 hour while stirring and 1 liter of water was added thereto. The pH of the mixture was adjusted to 4 with hydrochloric acid to deposit the crystals. The crystals were collected by filtration and recrystallized from acetonitrile to obtain 99 g of carboxylic acid. Then to this compound there were added 500 ml of benzene and 48 g of thionyl chloride and the mixture was refluxed for 2 hours. By distilling off the solvent and the excess thionyl chloride under a reduced pressure, 103 g of the above described carboxylic acid chloride was obtained.

Step (ii): Synthesis of 5-Amino-4-chloro-2-(2-dodecanesulfonamidobenzoylamino)phenol 28.2 g of 2-amino-4-chloro-5-nitrophenol was refluxed in 150 ml of acetonitrile and a solution containing 52.7 g of 2-dodecanesulfonamidobenzoyl chloride obtained in Step (i) above dissolved in 50 ml of acetonitrile was added to the mixture. After refluxing for 4 hours, the reaction mixture was cooled to deposit the crystals. The crystals were collected by filtration, washed with acetonitrile, and dried to yield 56 g thereof. The crystals were refluxed with stirring for 1 hour together with 60 g of reduced iron powder, 2 g of ammonium chloride, 50 g of water, and 500 ml of isopropanol. After removing the iron powder by filtration, the filtrate was poured into 2 liters of water to deposit the crystals. The crystals were collected by filtration and recrystallized from acetonitrile to obtain 36 g of the above described compound.

Step (iii): Synthesis of 8-Chloro-5-hydroxy-6-(2-dodecanesulfonamidobenzoylamino)-1,2,3,4-tetrahydro-3-methylquinazolin-2-one 36 g of the 5-amino-4-chloro-2-(2-dodecanesulfonamidobenzoylamino)phenol obtained in Step (ii) above was refluxed in 100 ml of acetonitrile and to the mixture was added dropwise 6.3 g of ethyl chloroformate. After refluxing for 4 hours, the reaction mixture was cooled to deposit the crystals. The crystals were collected by filtration and dried to yield 34 g thereof. 34 g of the crystals were dissolved in a solution composed of 4 ml of formalin, 8 ml of methylamine and 20 ml of methanol and the solution was refluxed for 5 hours with stirring. After the completion of the reaction, the reaction solution was cooled and poured into water. Acetic acid was added to the mixture to deposit the crystals. The crystals were collected by filtration, recrystallized from acetonitrile and dried to obtain 8.2 g of the above described coupler, having a melting point of 183° to 187° C.

Elemental Analysis: Calculated: C: 58.07, H: 6.79, N: 9.67. Found: C: 58.09, H: 6.85, N: 9.77.

The couplers of this invention are incorporated into the emulsion layers, generally in an amount of from about $2 \times 10^{-3}$ mol to $5 \times 10^{-1}$ mol, preferably $1 \times 10^{-2}$ mol to $5 \times 10^{-1}$ mol, per mol of silver.

The photographic emulsion prepared according to the present invention can contain a color image forming coupler other than the coupler according to the present invention. Non-diffusible couplers which contain a hydrophobic group, also referred to as a ballast group, in the molecule thereof are preferred as couplers. Couplers can be 4-equivalent or 2-equivalent to a silver ion. In addition, colored couplers providing a color correction effect, or couplers which release a development inhibitor upon development (so-called DIR couplers) can also be present therein. Also, couplers which provide a colorless product on coupling reaction can be employed.

Conventional open chain ketomethylene type couplers can be employed as yellow-color-forming couplers. Of these couplers, benzoyl acetanilide type and pivaloyl acetanilide type compounds are especially effective. Specific examples of yellow-color-forming couplers which can be employed are described, for example, in U.S. Pat. Nos. 2,875,057, 3,265,506, 3,408,194, 3,551,155, 3,582,322, 3,725,072 and 3,891,445, West German Pat. No. 1,547,868, West German Patent Application (OLS) Nos. 2,219,917, 2,261,361 and 2,414,006, British Pat. No. 1,425,020, Japanese Patent Publication No. 10783/76, Japanese Patent Application (OPI) Nos. 26133/72, 73147/73, 102636/76, 6341/75, 123342/75, 130442/75, 21827/76, 87650/75, 82424/77 and 115219/77.

Pyrazolone type compounds, indazolone type compounds, cyanoacetyl compounds, etc., can be employed as magenta-color-forming couplers, and particularly preferred couplers are pyrazolone type compounds. Specific examples of magenta-color-forming couplers which can be employed are those described, for example, in U.S. Pat. Nos. 2,600,788, 2,983,608, 3,062,653, 3,127,269, 3,311,476, 3,419,391, 3,519,429, 3,558,319, 3,582,322, 3,615,506, 3,834,908 and 3,891,445, West German Pat. No. 1,810,464, West German Patent Application (OLS) Nos. 2,408,665, 2,417,945, 2,418,959 and 2,424,467, Japanese Patent Publication No. 6031/65, Japanese Patent Application (OPI) Nos. 20826/76, 58922/77, 129538/74, 74027/74, 159336/75, 42121/77, 74028/74, 60233/75, 26541/76 and 55122/78.

Phenol type compounds, naphthol type compounds, etc., can be employed as cyan-color-forming couplers. Specific examples of cyan-color forming couplers which can be employed are those described, for example, in U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,767,411 and 4,004,929, German Patent Application (OLS) Nos. 2,414,830 and 2,454,329, Japanese Patent Application (OPI) Nos. 59838/73, 26034/76, 5055/73, 146828/76, 69624/77 and 90932/77.

Colored couplers which can be employed include those described, for example, in U.S. Pat. Nos. 3,476,560, 2,521,908 and 3,034,892, Japanese Patent Publication Nos. 2016/69, 22335/63, 11304/67 and 32461/69, Japanese Patent Application (OPI) Nos. 26034/76 and 42121/77, German Patent Application (OLS) No. 2,418,959.

DIR couplers which can be employed include those described, for example, in U.S. Pat. Nos. 3,227,554, 3,617,291, 3,701,783, 3,790,384 and 3,632,345, German Patent Application (OLS) Nos. 2,414,006, 2,454,301 and 2,454,329, British Pat. No. 953,454, Japanese Patent Application (OPI) Nos. 69624/77, 122335/74, Japanese Patent Publication No. 16141/76.

In addition to DIR couplers, other compounds which release development inhibitors upon development can also be present in the light-sensitive material. For example, such DIR compounds as are described in U.S. Pat. Nos. 3,297,445 and 3,379,529, German Patent Application (OLS) No. 2,417,914, Japanese Patent Application (OPI) Nos. 15271/77 and 9116/78, etc. can be employed.

Two or more kinds of the couplers described above can be incorporated in the same layer, or the same coupler compound can also be present in two or more layers.

Conventional methods, e.g., the method described in U.S. Pat. No. 2,322,027, can be employed to incorporate the couplers into the silver halide emulsion layers. For example, the couplers can be dissolved in phthalic acid alkyl esters (e.g., dibutyl phthalate, dioctyl phthalate, etc.), phosphoric acid esters (e.g., diphenyl phosphate, triphenyl phosphate, tricresyl phosphate, dioctylbutyl phosphate), citric acid esters (e.g., tributyl acetylcitrate), benzoic acid esters (e.g., octyl benzoate), alkylamides (e.g., diethyl laurylamide), fatty acid esters (e.g., dibutoxyethyl succinate, dioctyl azelate), etc.; or an organic solvent having a boiling point of from about 30° to 150° C. such as a lower alkyl acetate (e.g., ethyl acetate, butyl acetate, etc.), ethyl propionate, sec-butyl alcohol, methyl isobutyl ketone, $\beta$-ethoxyethyl acetate, methyl Cellosolve acetate, etc. Then the solution is dispersed in a hydrophilic colloid. The above-described organic solvents having a high boiling point and the above-described organic solvents having a low boiling point may be used as mixtures, if desired.

Furthermore, the dispersing method using a polymeric material as described in Japanese Patent Publication No. 39853/76, Japanese Patent Application (OPI) No. 59943/76 can also be used.

When couplers having an acid group, such as a carboxylic acid group, a sulfonic acid group, etc., are used, they can be incorporated in a hydrophilic colloid as an alkaline aqueous solution thereof.

The hydrophilic colloid layers of the light-sensitive elements prepared in accordance with the present invention can also contain UV absorbents. For example, benzotriazole compounds substituted with aryl groups (e.g., those described in U.S. Pat. No. 3,533,794), 4-thiazolidone compounds (e.g., those described in U.S. Pat. Nos. 3,314,794 and 3,352,681), benzophenone compounds (e.g., those described in Japanese Patent Application (OPI) No. 2784/71), cinnamic acid ester compounds (e.g., those described in U.S. Pat. Nos. 3,707,375 and 3,705,805), butadiene compounds (e.g., those described in U.S. Pat. No. 4,045,229) or benzoxazole compounds (e.g., those described in U.S. Pat. No. 3,700,455) can be employed. Furthermore, the compounds as described in U.S. Pat. No. 3,499,762, Japanese Patent Application (OPI) No. 48535/79 can also be used. UV absorbing couplers (e.g., $\alpha$-naphthol type cyan-color-forming couplers) and UV absorbing polymers can also be employed. These UV absorbents can also be mordanted in a specific layer(s), if desired.

The photographic emulsion used in this invention can be prepared using the methods described in, e.g., P. Glafkides, *Chimie et Physique Photographique*, Paul Montel, Paris (1967), G. F. Duffin, *Photographic Emulsion Chemistry*, The Focal Press, London (1966), V. L. Zelikman, et al., *Making and Coating Photographic Emulsions*, The Focal Press, London (1964), etc. That is, any of the acid method, the neutral method, the ammonia method and other methods can be used. Moreover, a soluble silver salt can be reacted with a soluble halogen salt using any of the single jet method, the double jet method, and a combination thereof.

A method in which grains are formed in the presence of an excess of silver ions (i.e., the so-called reverse mixing method) can also be used. An example of a useful mode of the double jet method is a method in which the pAg of the liquid phase in which the silver halide is to be produced is kept constant, that is, the so-called controlled double jet method. This method can provide silver halide emulsions having a regular crystal form and an almost uniform grain size.

Two or more silver halide emulsions which are separately prepared can be mixed and then used, if desired.

In the process of the formation of the silver halide grains or physical ripening, cadmium salts, zinc salts, lead salts, thallium salts, iridium salts or complex salts thereof, rhodium salts or complex salts thereof, iron salts or iron complex salts, and the like can be present.

Gelatin can advantageously be used as the binder or protective colloid for the photographic emulsion used in this invention. However, other hydrophilic colloids can be used as well. For example, proteins such as gelatin derivatives, graft polymers comprising gelatin and other high polymers, albumin, casein, etc.; cellulose derivatives such as hydroxyethyl cellulose, carboxymethyl cellulose, cellulose sulfates, etc.; saccharide derivatives such as sodium alginate, starch derivatives, etc.; and various synthetic hydrophilic high polymers of homo- or copolymers such as polyvinyl alcohol, polyvinyl alcohol partial acetal, poly-N-vinylpyrrolidone, polyacrylic acid, polymethacrylic acid, polyacrylamide, polyvinylimidazole, polyvinylpyrazole, etc., can be used as the binder or protective colloid for the photographic emulsion.

Acid-processed gelatin and enzyme-processed gelatin as described in Bull. Soc. Sci. Photo. Japan, No. 16, p. 30 (1966) can be used as well as lime-processed gelatin as the gelatin component. In addition, the hydrolyzed products of gelatin and enzyme-decomposed products of gelatin are also suitable. Suitable gelatin derivatives which can be used include those obtained by reacting gelatin with various compounds, such as acid halides, acid anhydrides, isocyanates, bromoacetic acid, alkanesultones, vinylsulfonamides, maleinimides, polyalkylene oxides, epoxy compounds, etc. Specific examples thereof are described in U.S. Pat. Nos. 2,614,928, 3,132,945, 3,186,846, 3,312,553, British Patents 861,414, 1,033,189, 1,005,784, Japanese Patent Publication No. 26845/67.

The above-described gelatin graft polymer may be obtained by grafting homo- or copolymers of vinyl monomers such as acrylic acid, methacrylic acid, the ester or amide derivatives thereof, acrylonitrile, styrene, etc., to gelatin. In particular, graft polymers with a polymer having some compatibility with gelatin, such as polymers of acrylic acid, methacrylic acid, acrylamide, methacrylamide, hydroxyalkyl methacrylates, etc., are preferred. Examples thereof are described in U.S. Pat. Nos. 2,763,625, 2,831,767, 2,956,884, etc. Typical synthetic hydrophilic materials are described in, e.g., German Patent Application (OLS) No. 2,312,708, U.S. Pat. Nos. 3,620,751, 3,879,205 and Japanese Patent Publication No. 7561/68.

For the purposes of preventing fog or stabilizing the photographic properties during preparation, storage, and/or photographic processing of light-sensitive materials, a variety of compounds can be incorporated into photographic emulsions used according to the present invention. For example, a wide variety of compounds which are known as anti-fogging agents or stabilizers, such as azoles, e.g., benzothiazolium salts, nitrobenzimidazoles, nitroindazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles, mercaptotetrazoles (especially 1-phenyl-5-mercaptotetrazole), etc.; mercaptopyrimidines; mercaptotriazines; thioketo compounds, such as oxazolinethione; azaindenes, e.g., triazaindenes, tetraazaindenes (especially 4-hydroxy-substituted (1,3,3a,7)tetraazaindenes), pentaazaindenes, etc.; benzenethiosulfonic acid, benzenesulfinic acid, benzenesulfonic amide, etc.; can be used. For example, the compounds as described in U.S. Pat. Nos. 3,954,474 and 3,982,947, Japanese Patent Publication No. 28660/77 can be used.

For the purposes of increasing sensitivity, increasing contrast, or accelerating development, the photographic emulsion layer(s) of the photographic light-sensitive element according to the present invention can contain other known additives, such as, for example, polyalkylene oxides or derivatives thereof such as ethers, esters, amines, etc., thioether compounds, thiomorpholine compounds, quaternary ammonium compounds, urethane derivatives, urea derivatives, imidazole derivatives, 3-pyrazolidones, etc. For example, such additives as described in U.S. Pat. Nos. 2,400,532, 2,423,549, 2,716,062, 3,617,280, 3,772,021, 3,808,003, British Pat. No. 1,488,991, etc.

The photographic emulsion of the present invention can also be spectrally sensitized with methine dyes or other dyes. Suitable dyes which can be employed include cyanine dyes, merocyanine dyes, complex cyanine dyes, complex merocyanine dyes, holopolar cyanine dyes, hemicyanine dyes, styryl dyes, and hemioxonol dyes. Of these dyes, cyanine dyes, merocyanine dyes and complex merocyanine dyes are particularly useful. Any conventionally utilized nucleus for cyanine dyes, such as basic heterocyclic nuclei, is applicable to these dyes. That is, a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus, a pyridine nucleus, etc., and further, nuclei formed by condensing alicyclic hydrocarbon rings with these nuclei and nuclei formed by condensing aromatic hydrocarbon rings with these nuclei, that is, an indolenine nucleus, a benzindolenine nucleus, an indole nucleus, a benzoxazole nucleus, a naphthoxazole nucleus, a benzothiazole nucleus, a naphthothiazole nucleus, a benzoselenazole nucleus, a benzimidazole nucleus, a quinoline nucleus, a etc., are appropriate. The carbon atoms of these nuclei can also be substituted.

In addition to merocyanine dyes and complex merocyanine dyes, those with nuclei having a keto-methyl structure, 5- or 6-membered heterocyclic nuclei such as a pyrazolin-5-one nucleus, a thiohydantoin nucleus, a 2-thioxazolidin-2,4-dione nucleus, a thiazolidin-2,4-dione nucleus, a rhodanine nucleus, a thiobarbituric acid nucleus, and so forth may also be used.

Further useful sensitizing dyes include those described in German Pat. No. 929,080, U.S. Pat. Nos. 2,231,658, 2,493,748, 2,503,776, 2,519,001, 2,912,329, 3,656,959, 3,672,897, 3,694,217, 4,025,349 and 4,046,572, British Pat. No. 1,242,588, Japanese Patent Publication Nos. 14030/69 and 24844/77, and so forth.

These sensitizing dyes can be employed individually, and can also be employed in combination. A combination of sensitizing dyes is often used, particularly for the purpose of supersensitization.

Representative examples thereof are described in U.S. Pat. Nos. 2,688,545, 2,977,229, 3,397,060, 3,522,052, 3,527,641, 3,617,293, 3,628,964, 3,666,480, 3,672,898, 3,679,428, 3,703,377, 3,769,301, 3,814,609, 3,837,862 and 4,026,707, British Pat. Nos. 1,344,281 and 1,507,803, Japanese Patent Publication Nos. 4936/68 and 12375/78, and Japanese Patent Application (OPI) Nos. 110618/77 and 109925/77.

The sensitizing dyes may be present in the emulsion together with dyes which themselves do not give rise to spectrally sensitizing effects but exhibit a supersensitizing effect or materials which do not substantially absorb visible light but exhibit a supersensitizing effect. For example, aminostilbene compounds substituted with a nitrogen-containing heterocyclic ring group (e.g., those described in U.S. Pat. Nos. 2,933,390 and 3,635,721), aromatic organic acid-formaldehyde condensates (e.g., those described in U.S. Pat. No. 3,743,510), cadmium salts, azaindene compounds, and the like, can be present. The combinations described in U.S. Pat. Nos. 3,615,613, 3,615,641, 3,617,295 and 3,635,721 are particularly useful.

The hydrophilic colloid layers of the light-sensitive material prepared according to the present invention can contain water-soluble dyes, as filter dyes, for purposes of preventing certain irradiations or other purposes. Such dyes include oxonol dyes, hemioxonol dyes, styryl dyes, merocyanine dyes, cyanine dyes and azo dyes. Of these dyes, oxonol dyes, hemioxonol dyes and merocyanine dyes are especially useful. Specific examples of such dyes which can be employed are described, for example, in British Pat. Nos. 584,609 and 1,177,429, Japanese Patent Application (OPI) Nos. 85130/73, 99620/74, 114420/74 and 108115/77, and U.S. Pat. Nos. 2,274,782, 2,533,472, 2,956,879, 3,148,187, 3,177,078, 3,247,127, 3,540,887, 3,575,704, 3,653,905, 3,718,472, 4,071,312 and 4,070,352.

The photographic emulsion layers and other hydrophilic colloid layers of the light-sensitive material prepared in accordance with the present invention can contain whitening agents, such as stilbenes, triazines, oxazoles, coumarins, etc. These agents can be water-soluble or can also be employed as a dispersion of water-insoluble whitening agents. Specific examples of fluorescent whitening agents are described in U.S. Pat. Nos. 2,632,701, 3,269,840 and 3,359,102, and British Pat. Nos. 852,075 and 1,319,763.

In the practice of the present invention, known color fading preventing agents as described below can be employed. These fading preventing agents can be used individually or in a combination of two or more thereof. Specific examples of known color fading preventing agents include, for example, hydroquinone derivatives as described in U.S. Pat. Nos. 2,360,290, 2,418,613, 2,675,314, 2,701,197, 2,704,713, 2,728,659, 2,732,300, 2,735,765, 2,710,801 and 2,816,028, British Pat. No. 1,363,921; gallic acid derivatives as described in U.S. Pat. Nos. 3,457,079 and 3,069,262; p-alkoxyphenols as described in U.S. Pat. Nos. 2,735,765 and 3,698,909, Japanese Patent Publication Nos. 20977/74 and 6623/77; p-oxyphenol derivatives as described in U.S. Pat. Nos. 3,432,300, 3,573,050, 3,574,627 and 3,764,337, Japanese Patent Application (OPI) Nos. 35633/77, 147434/77 and 152225/77; and bisphenol derivatives as described in U.S. Pat. No. 3,700,455, and so forth.

Light-sensitive elements prepared according to the present invention can also contain, as color fog preventing agents, hydroquinone derivatives, aminophenol derivatives, gallic acid derivatives, ascorbic acid derivatives, or the like. Specific examples of these agents are described in U.S. Pat. Nos. 2,360,290, 2,336,327, 2,403,721, 2,418,613, 2,675,314, 2,701,197, 2,704,713, 2,728,659, 2,732,300 and 2,735,765, Japanese Patent Application (OPI) Nos. 92988/75, 92989/75, 93628/75, 110337/75 and 146235/77, Japanese Patent Publication No. 23813/75, and so forth.

The present invention is also applicable to multilayer multicolor photographic materials containing layers sensitive to at least two different spectral wavelength ranges on a support. A multilayer color photographic material generally possesses at least one red-sensitive silver halide emulsion layer, at least one green-sensitive silver halide emulsion layer, and at least one blue-sensitive silver halide emulsion layer, respectively, on a support. The order of these layers can be varied if desired. Ordinarily, a cyan-forming coupler is present in a red-sensitive emulsion layer, a magenta-forming coupler is present in a green-sensitive emulsion layer, and a yellow-forming coupler is present in a blue-sensitive emulsion layer, respectively. However, if desired, different combinations can be employed.

Known methods can be used for processing the light-sensitive material according to the present invention. Known processing solutions can be used. The processing temperature can be between about 18° C. and about 50° C., in general, but temperatures lower than about 18° C. or higher than about 50° C. may be used, if desired. Either a development processing for forming silver images (black and white photographic processing) or a color photographic processing comprising developing processing for forming dye images can be employed, as desired.

The color developer generally comprises an alkaline aqueous solution containing a color developing agent. Suitable color developing agents which can be employed include known primary aromatic amine developing agents, e.g., phenylenediamines (e.g., 4-amino-N,N-diethylaniline, 3-methyl-4-amino-N,N-diethylaniline, 4-amino-N-ethyl-N-$\beta$-hydroxyethylaniline, 3-methyl-4-amino-N-ethyl-N-$\beta$-hydroxyethylaniline, 3-methyl-4-amino-N-ethyl-N-$\beta$-methanesulfamidoethylaniline, 4-amino-3-methyl-N-ethyl-N-$\beta$-methoxyethylaniline, etc.).

In addition, developing agents described in L. F. A. Mason, *Photographic Processing Chemistry*, at pages 226 to 229, Focal Press (1966), U.S. Pat. Nos. 2,193,015 and 2,592,364, Japanese Patent Application (OPI) No. 64933/73, etc., can be employed.

The color developers can also contain pH buffering agents, such as sulfites, carbonates, borates and phosphates of alkali metals, developing inhibitors or antifogging agents such as bromides, iodides, organic antifogging agents, etc. In addition, if desired, the color developers can also contain water softeners, preservatives such as hydroxylamine; organic solvents such as benzyl alcohol, diethylene glycol, etc.; developing accelerators such as polyethylene glycol, quaternary ammonium salts, amines; dye-forming couplers; competing couplers; fogging agents such as sodium borohydride; auxiliary developers such as 1-phenyl-3-pyrazolidone; viscosity-imparting agents; polycarboxylic acid type chelating agents described in U.S. Pat. No. 4,083,723; anti-oxidizing agents as described in German Patent Application (OLS) No. 2,622,950; and the like.

The photographic emulsion layers after color development are generally bleach-processed. Bleach processing can be performed at the same time as fixing, or separately therefrom. Suitable bleaching agents which can be employed are compounds of polyvalent metals such as iron (III), cobalt (III), chromium (VI), copper (II), etc., peracids, quinones, nitroso compounds, etc. Specific examples include ferricyanides; bichromates; organic complexes of iron (III) or cobalt (III), for example complexes of aminopolycarboxylic acids such as ethylenediaminetetraacetic acid, nitrilotriacetic acid, 1,3-diamino-2-propanol tetraacetic acid, etc.; or complexes of organic acids such as citric acid, tartaric acid, malic acid, etc.; persulfates; permanganates; nitroso-phenol; etc. Of these compounds, potassium ferricyanide, sodium ethylenediaminetetraacetate iron (III) and ammonium ethylenediaminetetraacetate iron (III) are particularly preferred. Ethylenediaminetetraacetate iron (III) complex is useful both in a bleaching solution and in a mono bath bleach-fixing solution.

Bleaching solutions or bleach-fixing solutions can contain various additives, including bleach accelerating agents as described in U.S. Pat. Nos. 3,042,520 and 3,241,996, Japanese Patent Publication Nos. 8506/70 and 8836/70, thioether compounds as described in Japanese Patent Application (OPI) No. 65732/78, and the like.

The present invention is explained in greater detail with reference to the example below, but the present invention should not be construed as being limited thereto.

EXAMPLE 1

A solution prepared by heating, at 50° C., a mixture of 25 g of Coupler (1), 25 g of trioctyl phosphate and 50 ml of ethyl acetate was added to 250 ml of an aqueous solution containing 25 g of gelatin and 1.0 g of sodium dodecylbenzenesulfonate with stirring. The mixture was then passed 5 times through a preheated colloid mil, by which the coupler was finely dispersed together with the solvents.

The whole amount of the dispersion thus prepared was added to 1.0 kg of a photographic emulsion containing 54 g of silver iodobromide and 60 g of gelatin and to the mixture, 80 ml of a 2% aqueous solution of 4,6-dichloro-2-hydroxytriazine as a hardener was added. The pH of the mixture was adjusted to 6.0 and coated on a cellulose triacetate film base at a dry thickness of 7.0 microns. This was designated as Sample A.

In place of Coupler (1) described above, using the equimolar amount of Couplers (5), (8) and (11) according to the present invention films were prepared in an analogous mannner as described above for Sample A. These are designated as Samples B, C and D, respectively.

For comparison, using the equimolar amount of Comparison Couplers (101) and (102) described below in place of Coupler (1) described above, films were prepared in an analogous manner as described for Sample A. These are designated as Samples E and F, respectively.

Comparison Coupler (101)

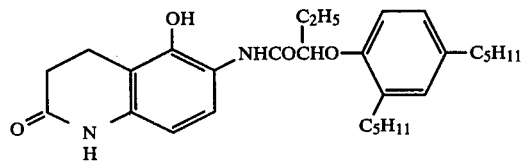

Comparison Coupler (102)

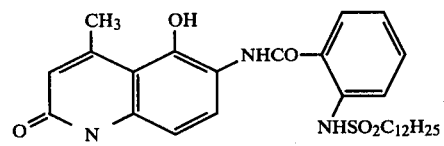

These films were exposed continuously using a sensitometric wedge and subjected to the following processing steps.

| Processing Step | Temperature (°C.) | Time |
|---|---|---|
| 1. Color development | 33 | 3 min. 30 sec. |
| 2. Bleach-fixing | 33 | 1 min. 30 sec. |
| 3. Washing with water | 25 to 30 | 2 min. 30 sec. |

Each of the processing solutions used in the color development processing steps had the following composition.

| Color Developer Solution | |
|---|---|
| Benzyl Alcohol | 15 ml |
| Diethylene Glycol | 8 ml |
| Ethylenediaminetetraacetic Acid | 5 g |
| Sodium Sulfite | 2 g |
| Anhydrous Potassium Carbonate | 30 g |
| Hydroxylamine Acetate | 3 g |
| Potassium Bromide | 0.6 g |
| 4-Amino-N—ethyl-N—(β-methane-sulfonamidoethyl)-m-toluidine Sesquisulfate Monohydrate | 5 g |
| Water to make (pH 10.2) | 1 l |
| Bleach-Fixing Solution | |
| Ethylenediaminetetraacetic acid | 2 g |
| Ferric Salt of Ethylenediaminetetraacetate | 40 g |
| Sodium Sulfite | 5 g |
| Ammonium Thiosulfate | 70 g |
| Water to make | 1 l |

The absorption spectrum of each sample thus processed was measured and the results obtained are shown in Table 1 below.

TABLE 1

| Film Sample | Coupler | Absorption Maximum (mµ) | Width of Absorption at Half of Maximum Density (mµ) | Absorbance at 450 µm Absorbance at Absorption Maximum |
|---|---|---|---|---|
| A | (1) Present Invention | 653 | 137 | 0.05 |
| B | (5) Present Invention | 651 | 138 | 0.05 |
| C | (8) Present Invention | 649 | 132 | 0.04 |
| D | (11) Present Invention | 650 | 132 | 0.04 |
| E | (101) Comparison | 632 | 137 | 0.07 |
| F | (102) Comparison | 647 | 135 | 0.21 |

It is apparent from the results shown in Table 1 above that the couplers according to the present invention provide color images having an absorption maximum at a range from 645 mµ to 655 mµ which is preferred in view of color reproduction and a small undesirable subsidiary absorption. Thus the couplers are advantageous for color reproduction.

Further, each film thus processed was subjected to testing with respect to fastness to light and fastness to heat. More specifically, the samples were left for 6 weeks in a dark place at 60° C. and 70% RH and the samples were irradiated for 6 days in a xenon test apparatus (100,000 luxes) and a density reduction rate of a sample in the area where initial density was 1.0 was measured. The results obtained are shown in Table 2 below.

TABLE 2

| Sample | Coupler | 60° C., 70% RH 6 Weeks | Light (Xenon) 6 Days |
|---|---|---|---|
| A | (1) Present Invention | 4% | 5% |
| B | (5) Present Invention | 5% | 6% |
| C | (8) Present Invention | 3% | 6% |
| D | (11) Present Invention | 2% | 4% |
| E | (101) Comparison | 8% | 9% |
| F | (102) Comparison | 10% | 8% |

As is apparent from the results shown in Table 1 above Comparison Couplers (101) and (102) which have a relatively good color image fastness are still not preferred in view of color reproduction since the color image formed from Comparison Coupler (101) has the absorption maximum at a relatively short wave length range and the color image formed from Comparison Coupler (102) has the subsidiary absorption. On the contrary, the couplers according to the present invention can provide the color images which are not only preferable in view of the absorption maximum wave length but also excellent with respect to the fastness to light and heat.

EXAMPLE 2

On a paper support both surfaces of which were laminated with polyethylene were coated a first layer (undermost layer) to a sixth layer (uppermost layer) as shown in the Table below in order (coating solutions thereof were prepared in an analogous manner as described in Example 1) to prepare a multilayer color photographic light-sensitive material which is designated Sample G. In the Table below, the coating amounts are set forth in mg/m².

| | |
|---|---|
| Sixth Layer: (Protective layer) | Gelatin (1,500 mg/m²) |
| Fifth Layer: (Red-sensitive layer) | Silver chlorobromide emulsion (Silver bromide: 50 mol %; silver: 300 mg/m²) Gelatin (1,500 mg/m²) Cyan coupler*¹ (500 mg/m²), Coupler solvent*² (250 mg/m²) |
| Fourth Layer: (Ultraviolet light-absorbing layer) | Gelatin (1,200 mg/m²), Ultraviolet light-absorbing agent*³ (1000 mg/m²), Ultraviolet light-absorbing agent solvent*² (250 mg/m²) |
| Third Layer: (Green-sensitive layer) | Silver chlorobromide emulsion (Silver bromide: 50 mol %; silver: 450 mg/m²) Gelatin (1,500 mg/m²), Magenta coupler*⁴ (400 mg/m²), Coupler solvent*⁵ (200 mg/m²) |
| Second Layer: (Interlayer) | Gelatin (1,000 mg/m²) |
| First Layer (Blue-sensitive layer) | Silver chlorobromide emulsion (Silver bromide: 80 mol %; silver: 450 mg/m²) Gelatin (1,500 mg/m²) Yellow coupler*⁶ (500 mg/m²) Coupler solvent*⁷ (250 mg/m²) |
| Support: | Paper support both surfaces of which were laminated with polyethylene |

*¹Cyan coupler:
2-[α-(2,4-Di-tert-amylphenoxy)butanamido]-4,6-dichloro-5-methylphenol [Comparison Coupler (103)]
*²Coupler solvent: Di-n-butyl phthalate
*³Ultraviolet light-absorbing agent:
2-(2-Hydroxy-3-sec-butyl-5-tert-butylphenyl)benzotriazole
*⁴Magenta coupler:
1-(2,4,6-Trichlorophenyl)-3-(2-chloro-5-tetradecan-amido)anilino-2-pyrazolin-5-one
*⁵Coupler solvent: Tri-o-cresyl phosphate
*⁶Yellow coupler: α-Pivaloyl-α-(2,4-dioxo-5,5-dimethyl oxazolidin-3-yl)-2-chloro-5-[α-(2,4-di-tert-amylphenoxy)butanamido]acetanilide
*⁷Coupler solvent: Tri-o-cresyl phosphate In place of Comparison Coupler (103) in the fifth layer of Sample (G) described above, using Couplers (1) and (11) according to the present invention, films were prepared. These are designated Samples (H) and (I), respectively.

These samples were subjected to the same development processing as described in Example 1 and tested with respect to fastness to light and fastness to heat. More specifically, the samples were left for 2 weeks in an almost dry atmosphere at 80° C., the samples were left for 4 weeks in a dark place at 60° C. and 70% RH, and the samples were irradiated for 6 days in a xenon test apparatus (100,000 luxes) and a density reduction rate (%) of the cyan color image in the area where initial density was 1.0 was measured. The results obtained are shown in Table 2 below.

TABLE 3

| Film Sample | Coupler | 80° C. 2 Weeks | 60° C., 70% RH 4 Weeks | Light (Xenon) 6 Days |
|---|---|---|---|---|
| G | (103) Comparison | 35 | 13 | 25 |
| H | (1) Present Invention | 8 | 4 | 9 |
| I | (11) Present Invention | 5 | 3 | 7 |

It is apparent from the results shown in Table 3 above that the dye images formed from the cyan couplers according to the present invention are extremely fast both to light and heat.

While the invention has been described in detail and with reference to specific embodiments thereof, it will be apparent to one skilled in the art that various changes and modifications can be made therein without departing from the spirit and scope thereof.

What is claimed is:

1. A color photographic light-sensitive material comprising a support having coated thereon at least one silver halide emulsion layer, the color photographic light-sensitive material containing a cyan dye forming coupler represented by the following general formula (I):

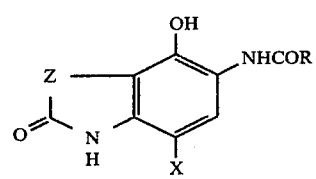

wherein Z represents

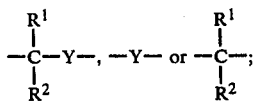

R represents a substituted or unsubstituted alkyl group, a substituted or unsubstituted aryl group or a substituted heterocyclic group; X represents a hydrogen atom or a group capable of being released upon an oxidative coupling reaction with a developing agent; Y represents

—O— or —S—; $R^1$ and $R^2$, which may be the same or different, each represents a halogen atom, a substituted or unsubstituted alkyl group, a substituted or unsubstituted aryl group, a substituted or unsubstituted alkoxy group, a substituted or unsubstituted alkoxycarbonyl group, a substituted or unsubstituted alkylcarbonyl group, a substituted or unsubstituted arylcarbonyl group, a substituted or unsubstituted carbamoyl group, a substituted or unsubstituted acylamino group or a nitryl group or $R^1$ and $R^2$ together represents an oxo group; and $R^3$ represents a hydrogen atom, a substituted or unsubstituted alkyl group or a substituted or unsubstituted aryl group.

2. A color photographic light-sensitive material as claimed in claim 1, wherein the alkyl group represented by R is an alkyl group having from 1 to 22 carbon atoms.

3. A color photographic light-sensitive material as claimed in claim 1, wherein the substituent for the alkyl group, the aryl group or the heterocyclic group represented by R is selected from an alkyl group, an aryl group, an alkoxy group, an aryloxy group, a carboxy group, an alkylcarbonyl group, an arylcarbonyl group, an alkoxycarbonyl group, an aryloxycarbonyl group, an acyloxy group, a sulfamoyl group, a carbamoyl group, a sulfonamido group, an acylamino group, a diacylamino group, a sulfonyl group, a hydroxy group, a cyano group, a nitro group and a halogen atom.

4. A color photographic light-sensitive material as claimed in claim 1, wherein the substituent for the alkyl moiety and the aryl moiety represented by $R^1$, $R^2$ and $R^3$ is selected from an alkyl group, an aryl group, an alkoxy group, an aryloxy group, a carboxy group, an alkylcarbonyl group, an arylcarbonyl group, an alkoxycarbonyl group, an aryloxycarbonyl group, an acyloxy group, a sulfamoyl group, a carbamoyl group, a sulfonamido group, an acylamino group, a diacylamino group, a sulfonyl group, a hydroxy group, a cyano group, a nitro group and a halogen atom.

5. A color photographic light-sensitive material as claimed in claim 1, wherein X represents a hydrogen atom.

6. A color photographic light-sensitive material as claimed in claim 1, wherein X represents a halogen atom, an alkoxy group, an aryloxy group, an acyloxy group, a sulfonyloxy group, an acylamino group, a sulfonylamino group, an alkoxycarbonyloxy group, an aryloxycarbonyloxy group, or an imido group.

7. A color photographic light-sensitive material as claimed in claim 1, wherein the cyan dye forming coupler is represented by the following general formula (II), (III), (IV) or (V)

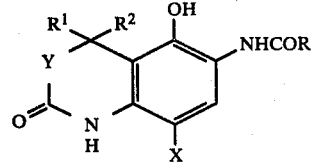

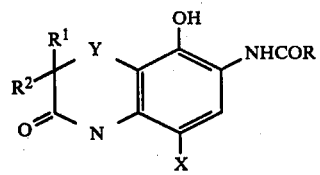

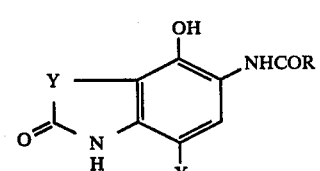

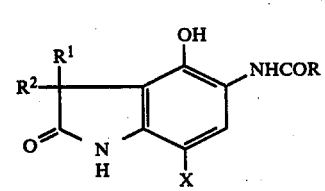

wherein R, $R^1$, $R^2$, Y and X each has the same meaning as defined in claim 1.

8. A color photographic light-sensitive material as claimed in claim 7, wherein R represents an alkyl group or an aryl group.

9. A color photographic light-sensitive material as claimed in claim 7, wherein Y represents

or —O—, and $R^3$ represents a hydrogen atom, an alkyl group or an aryl group.

10. A color photographic light-sensitive material as claimed in claim 7, wherein $R^1$ represents a hydrogen atom, an alkyl group or an aryl group.

11. A color photographic light-sensitive material as claimed in claim 7, wherein $R^2$ represents a hydrogen atom, an alkyl group or an aryl group.

12. A color photographic light-sensitive material as claimed in claim 7, wherein X represents a hydrogen atom or a chlorine atom.

13. A color photographic light-sensitive material as claimed in claim 1, wherein the cyan dye forming coupler is present in a silver halide emulsion layer.

14. A color photographic light-sensitive material as claimed in claim 13, wherein the silver halide emulsion layer is a red sensitive silver halide emulsion layer.

15. A color photographic light-sensitive material as claimed in claim 14, wherein the photographic material further includes a blue sensitive silver halide emulsion layer and a green sensitive silver halide emulsion layer.

16. A color photographic light-sensitive material as claimed in claim 15, wherein the blue sensitive silver halide emulsion layer contains a yellow color forming coupler and the green sensitive silver halide emulsion layer contains a magenta color forming coupler.

17. A method of forming a color image comprising developing an imagewise exposed a color photographic light-sensitive material comprising a support having coated thereon at least one silver halide emulsion layer, the color photographic light-sensitive material containing a cyan dye forming coupler represented by the following general formula (I):

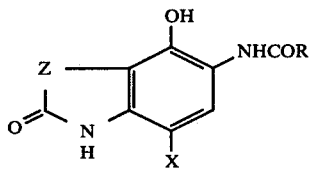

wherein Z represents

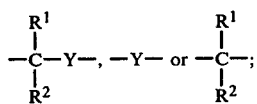

R represents a substituted or unsubstituted alkyl group, a substituted or unsubstituted aryl group or a substituted or unsubstituted heterocyclic group; X represents a hydrogen atom or a group capable of being released upon an oxidative coupling reaction with a developing agent; Y represents

—O— or —S—; $R^1$ and $R^2$, which may be the same or different, each represents a halogen atom, a substituted or unsubstituted alkyl group, a substituted or unsubstituted aryl group, a substituted or unsubstituted alkoxy group, a substituted or unsubstituted alkoxycarbonyl group, a substituted or unsubstituted alkylcarbonyl group, a substituted or unsubstituted arylcarbonyl group, a substituted or unsubstituted carbamoyl group, a substituted or unsubstituted acylamino group or a nitryl group or $R^1$ and $R^2$ together represents an oxo group; and $R^3$ represents a hydrogen atom, a substituted or unsubstituted alkyl group or a substituted or unsubstituted aryl group with an alkaline aqueous solution containing an aromatic amine developing agent.

18. A method of forming a color image as claimed in claim 17, wherein the photographic material, after development, is subjected to processing in a bleach-fixing solution.

19. A method of forming a color image as claimed in claim 18, wherein the bleach-fixing solution contains an ethylenediaminetetraacetate iron (III) complex.

* * * * *